(12) United States Patent
Gorman

(10) Patent No.: US 8,414,834 B2
(45) Date of Patent: Apr. 9, 2013

(54) TREE SCENTS

(76) Inventor: Kimm E. Gorman, Columbus, OH (US)

( * ) Notice: Subject to any disclaimer, the term of this patent is extended or adjusted under 35 U.S.C. 154(b) by 136 days.

(21) Appl. No.: 13/028,817

(22) Filed: Feb. 16, 2011

(65) Prior Publication Data

US 2011/0198409 A1 Aug. 18, 2011

Related U.S. Application Data

(60) Provisional application No. 61/305,179, filed on Feb. 17, 2010.

(51) Int. Cl.
*A62B 7/08* (2006.01)
*A61L 9/00* (2006.01)

(52) U.S. Cl.
USPC ........... 422/125; 422/120; 422/123; 422/124; 422/5

(58) Field of Classification Search ................... 422/120, 422/122, 124, 5, 123, 125
See application file for complete search history.

(56) References Cited

U.S. PATENT DOCUMENTS

| | | | | |
|---|---|---|---|---|
| 5,220,636 A * | 6/1993 | Chang | ............................ | 392/392 |
| 5,233,680 A * | 8/1993 | Fussell | ........................... | 392/390 |
| 5,455,750 A * | 10/1995 | Davis et al. | .................... | 362/123 |
| 5,624,230 A * | 4/1997 | Taylor et al. | ...................... | 416/5 |
| 5,805,768 A * | 9/1998 | Schwartz et al. | ............. | 392/390 |
| 6,602,475 B1 * | 8/2003 | Chiao | ............................ | 422/124 |
| 6,713,024 B1 * | 3/2004 | Arnell et al. | ................... | 422/124 |
| 6,783,117 B2 * | 8/2004 | Wohrle | ............................ | 261/26 |
| 6,834,847 B2 * | 12/2004 | Bartsch et al. | ................... | 261/26 |
| 7,469,844 B2 * | 12/2008 | Conway et al. | ............. | 239/102.2 |
| 7,622,073 B2 * | 11/2009 | Schramm et al. | .................. | 422/5 |
| 2002/0005437 A1 * | 1/2002 | Ketcha et al. | .................... | 239/13 |
| 2004/0197221 A1 * | 10/2004 | Stanley, III | ........................ | 422/5 |
| 2006/0018786 A1 * | 1/2006 | Tolman et al. | .................... | 422/5 |
| 2007/0025888 A1 * | 2/2007 | Gupte et al. | ................... | 422/125 |
| 2011/0027124 A1 * | 2/2011 | Albee et al. | ......................... | 422/5 |

* cited by examiner

*Primary Examiner* — Regina M Yoo
(74) *Attorney, Agent, or Firm* — Porter Wright Morris & Arthur, LLP.

(57) ABSTRACT

A scent dispersing device for use with an artificial tree having a hollow trunk, the device comprising a disk comprising a container for housing a replaceable fragrance cartridge and an energizable heater in communication with the cartridge. When the heater is energized, the cartridge emits a fragrance through openings in the disk. The invention comprises a motorized fan, such that when the fan operates, air is forced into the hollow trunk and through at least one disk located at the bottom or between sections of the assembled trunk and fragrance is forced through openings in the disk or holes in the trunk. The invention includes a tree stand that houses a fan, lighting, and audio each wired to a control panel and timer connected to an energy source.

10 Claims, 6 Drawing Sheets

TREE SCENTS

This application claims benefit to provisional patent application 61/305,179 filed Feb. 17, 2010.

FIELD OF THE INVENTION

The present invention relates generally to scenting devices and, more particularly, to an improved heated device for generating and dispersing a desired scent or fragrance from an artificial tree or stand.

BACKGROUND OF THE INVENTION

Holidays are celebrated around the world. Millions of Americans celebrate Christmas every year through gift giving, visiting friends and relatives, and decorating. Consumers spent nearly $13.7 billion during the 2002 online holiday shopping seasons, according to a report from The Goldman Sachs Group, Inc., Harris Interactive, and Nielsen/NetRatings.

Everyone who celebrates Christmas looks forward not only to the religious significance of the season but also to all the traditions of this holiday. Perhaps the most important and memorable of all the Christmas traditions is decorating.

The Christmas tree is perhaps the most ornate decoration for the holidays. The tree is the center of attention in any room. People spend a great deal of time decorating the tree and deciding where it will be displayed. According to the results of a survey conducted by Unity Marketing, ("Holiday Decorating Destined to Be Big this Season," Press Release of Unity Marketing, Oct. 1, 2003) of 1,000 U.S. households that decorate their home for different holidays, people decorate in order to get them in the mood for a happy, memorable celebration. Nearly three fourths of decorators agree with the statement "Decorating my home gets me in the mood for celebrating and having fun." While decorating looks into the future, it is also nostalgic as bringing out decorations from the past rekindles fond memories. Nearly 70% of decorators agree, "I love to bring out my favorite decorations from years gone by: they are like old 'friends' and bring back wonderful memories."

Generally, trimming the Christmas tree is a family time in which all members, even the youngest, participate. Putting up lights, trimming the tree, and displaying all the Christmas memorabilia, seems to stir up memories of past Christmases. Perhaps the ornament was the first one the couple bought after they were married, maybe a close relative who has since passed on gave the ornament as a gift, or the ornament could have been the first one that the children made themselves. Whatever the case may be, Christmas is a very decorative, family oriented time.

Ninety percent of Americans consider Christmas their favorite holiday. Of those who celebrate, 85% have a tree, with 34% displaying an artificial tree ("U.S. Consumers Purchase More Real Trees," National Christmas Tree Association, realchristmastrees.org, Feb. 28, 2005). A problem exists with artificial Christmas trees. The smell of a real tree that provides nostalgic memories is not included in a plastic tree. Some artificial trees may even emit a "plastic" odor that counters the memories of childhood. To overcome this problem, people displaying artificial trees have resorted to spraying scents, candles, or using pine boughs in proximity to mimic the smell of a real Christmas tree. Other fragrances are employed to create a mood, energize the senses, or enhance a meditative moment. Currently, candles, diffusers, oils, potpourris, blended closet fresheners, linen sprays, and the like provide fragrance for homes and offices.

Problems occur with existing remedies. Pine bough wreaths or garlands leave dropped needles throughout the home or office. Burning candles can be dangerous. Sprays are expensive and typically do not last.

A need exists for an unobtrusive device to provide a pleasing scent for an artificial Christmas tree to eliminate the need for live trees, wreaths, burning candles or expensive sprays. A need exists for a device to create a desired atmosphere in a home by 'decorating' a room with a fragrance rather than using it simply for functional purposes. Adding other elements, such as music, lights, and the like would meet many needs to create nostalgic memories.

SUMMARY OF THE INVENTION

The present invention is an improved holiday device designed to dispense a scent and add other elements, such as lighting and music. The invention supplements the holiday décor and fills the room with a pleasing aroma that may influence the members' moods due to aromatherapy.

The present invention is a scent dispersing device for use with an artificial tree. The device comprises a disk having a hollow container for housing a replaceable fragrance cartridge. The disk has openings to allow the fragrance to disperse from the disk. The disk is placed either in a hollow trunk section of the tree, between sections or at an opening of a section of the tree. The device comprises an energizable heater in communication with the cartridge such that when the heater is energized, the fragrance cartridge emits a fragrance.

In an embodiment, the disks are located between a first and second section and the second and a third section of a typical 3-section artificial Christmas tree. One skilled in the art would readily understand that a tree having more sections would allow more disks. The device comprises an energizable fan that, when energized, blows fragrance out of the openings of the disk.

In an embodiment, the device comprises a stand having an opening for a bottom end of the tree trunk. The stand comprises an energizable fan that, when energized, blows air through the trunk, which forces air through the cartridges and carries fragrance out of the openings of the disks. Disks are placed in the stand (which may be in addition to the trunk) so that the blower forces air through the cartridge and out of openings and/or holes located in the trunk. The stand optionally comprises a container for holding replacement cartridges.

The device comprises elements, such as an energizable illuminating source, an energizable audio producer, an energy source, and a mechanical rotator, that are connected to a controller and a timer, either individually or as a group. The disks are optionally electrically connected to one another. The disks may also be incorporated within other artificial holiday decorations, such as but not limited to a wreath, garland, and the like.

The invention is used with standard artificial trees, such as those used with the Christmas holiday. Any tree is acceptable, including various heights, widths, and colors. The present invention is virtually hidden from view and eliminates the need for live trees or cut pine bough wreaths or garlands that may leave dropped pine needles throughout the home or office. The invention eliminates burning candles as well as live trees that can be a fire hazard and can be dangerous. The invention avoids the added expense of sprays, and provides a convenient single source for Christmas music, lighting and scents.

As used herein, "approximately" means within plus or minus 25% of the term it qualifies. The term "about" means between ½ and 2 times the term it qualifies.

The compositions and methods of the present invention can comprise, consist of, or consist essentially of the essential elements and limitations of the invention described herein, as well as any additional or optional ingredients, components, or limitations described herein or otherwise useful in compositions and methods of the general type as described herein.

Numerical ranges as used herein are intended to include every number and subset of numbers contained within that range, whether specifically disclosed or not. Further, these numerical ranges should be construed as providing support for a claim directed to any number or subset of numbers in that range or to be limited to the exact conversion to a different measuring system, such, but not limited to, as between inches and millimeters.

All references to singular characteristics or limitations of the present invention shall include the corresponding plural characteristic or limitation, and vice versa, unless otherwise specified or clearly implied to the contrary by the context in which the reference is made.

All references to gender include reference to both male and female.

All combinations of method or process steps as used herein can be performed in any order, unless otherwise specified or clearly implied to the contrary by the context in which the referenced combination is made.

Terms such as "top," "bottom," "right," "left," "above", "under", "side" and the like are words of convenience and are not to be construed as limiting.

DETAILED DESCRIPTION OF THE INVENTION

The present invention comprises a scent dispersing device for use with an artificial tree. Referring now to the Figures, the present invention is a disk 1 that is included in or on an artificial tree or stand to release an incorporated concentrated scent. The disk is produced from a die cast metal or a heat resistant molded plastic. Any hardenable material, such as conventional thermoplastic materials are suitable, including but not limited to polymers such as polyethylene and acrylonitrile butadiene styrene (ABS).

The disk 1 comprises a hollow portion for housing a replaceable fragrance cartridge 2. The disk 1 comprises an energizable heater 12 that heats the cartridge. The disk has openings 10 a-n to allow the fragrance to disperse from the disk, so that when the heater is energized, a fragrance from the fragrance cartridge is emitted from the disk.

Figure 1:
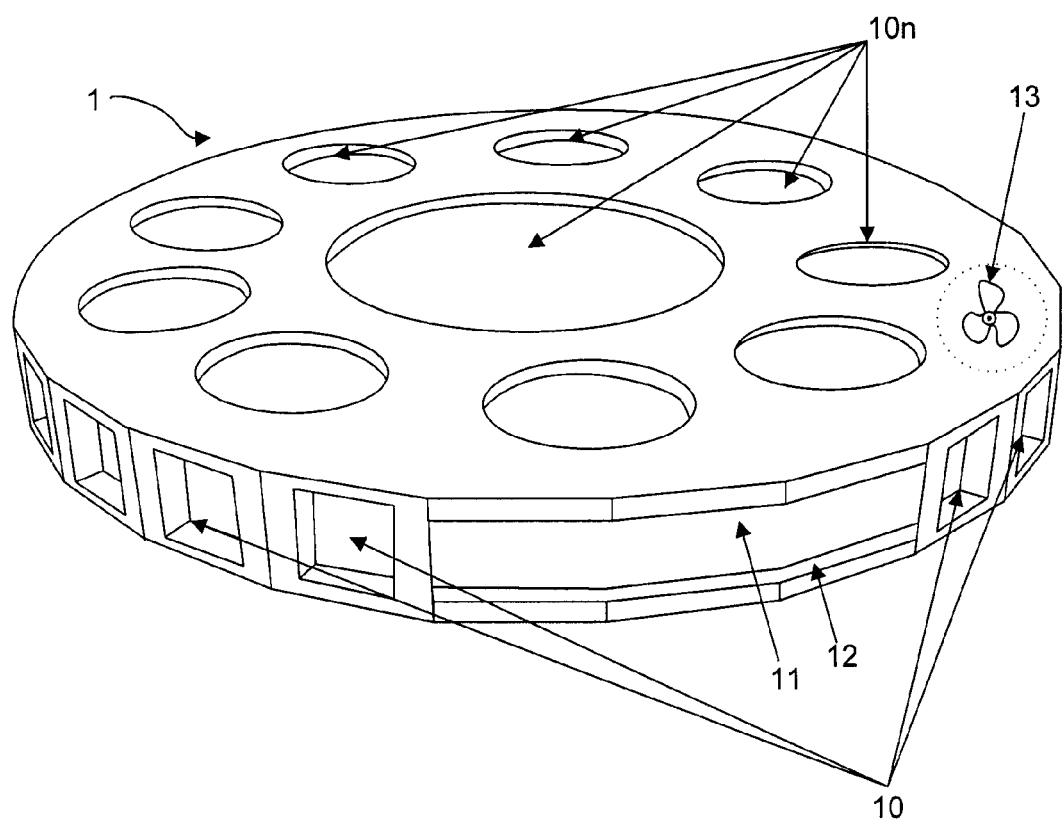
FIG. 1 is a perspective view of an embodiment of the invention showing the disk.
Figure 2:
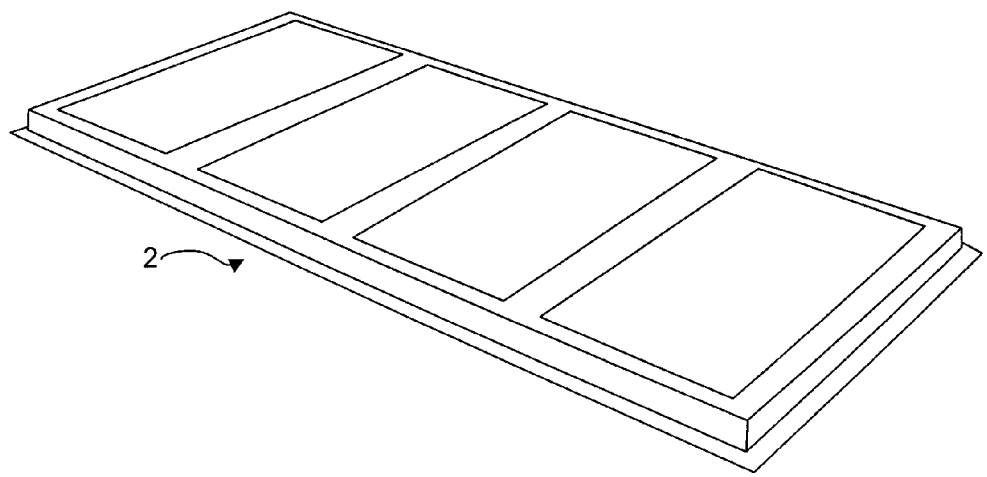
FIG. 2 is a perspective view of an embodiment of the invention showing a fragrance cartridge.

As shown in FIG. 1, the disk is shaped to appear as part of the tree trunk and fit the trunk segments of the tree and between the tree and the stand. In the preferred embodiment, the disk is disk-shaped, but any suitable shape may be substituted, including square, rectangular, trapezoid and the like. The disks may be differently sized to adapt to an artificial tree trunk that is tapered. The disk 1 comprises a rigid shell with many openings 10a-n to allow the fragrance to emit from the disk. The openings may be round or square or slits, etc. The disk includes an opening 11 to insert a fragrance cartridge.

The disk comprises a heater 12 or heating unit. The heater is any conventional heating device that provides sufficient temperature to volatilize the fragrance. The heater is preferable in contact with the fragrance cartridge. Optionally, the disk comprises a fan 13. When the fan operates, air is forced through the fragrance cartridge and out openings in the disk. The heater and fan are powered by a standard electric cord featuring a male plug 42 or powered by batteries. A battery compartment may be included in the disk. Alternately, the disks may include female electrical connections to connect more than one disk in series. The disk may be electrically wired for connection to another disk, extension cord, or outlet.

Figure 3:
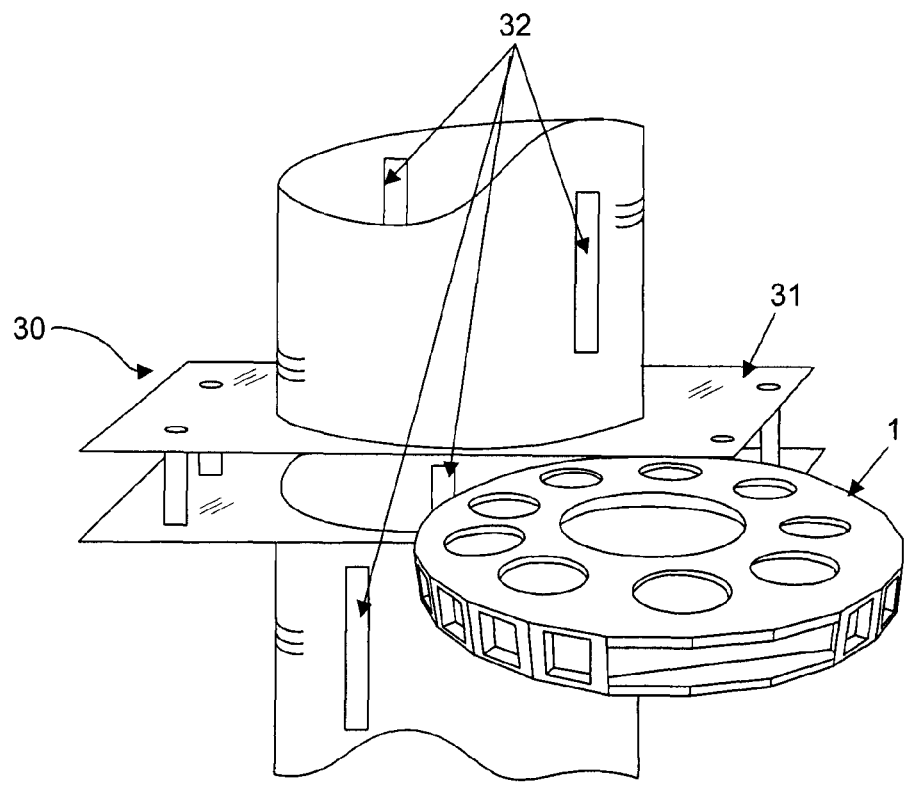
FIG. 3 is a perspective view of an embodiment of the invention showing the disk being inserted between sections of the tree trunk.
Figure 4:
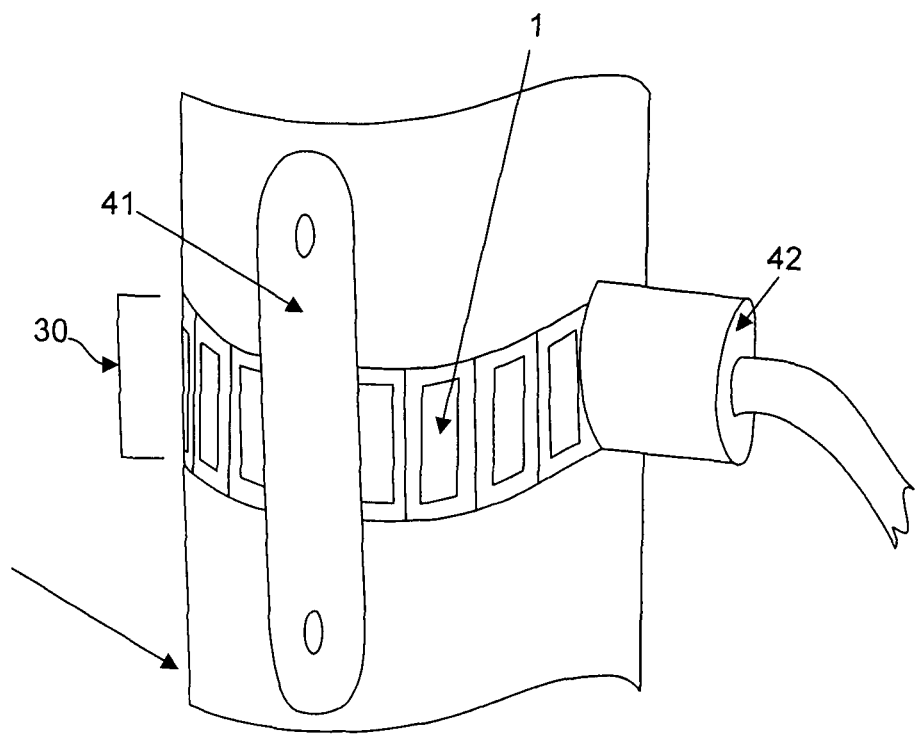
FIG. 4 is a perspective view of an alternate embodiment of the invention showing the disk inserted between sections of the tree trunk.

In embodiments depicted in FIGS. 3 and 4, the device is located in a compartment 30 in the artificial tree trunk. The compartment 30 may include additional stabilizing features 31, 41.

Figure 5:
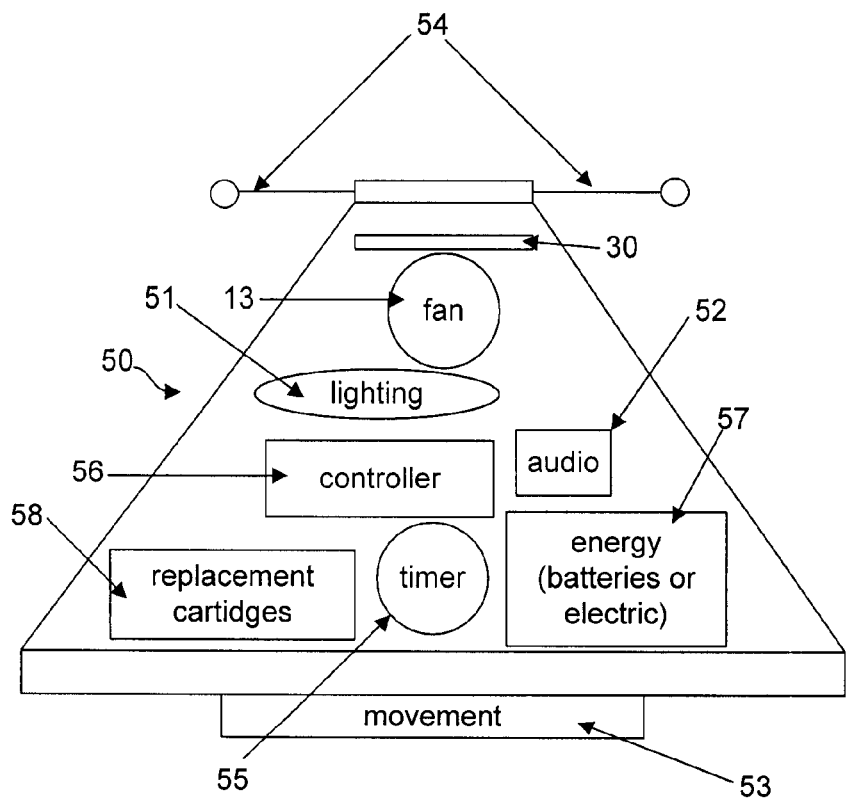
FIG. 5 is a diagram of the elements shown in a stand.
Figure 6:
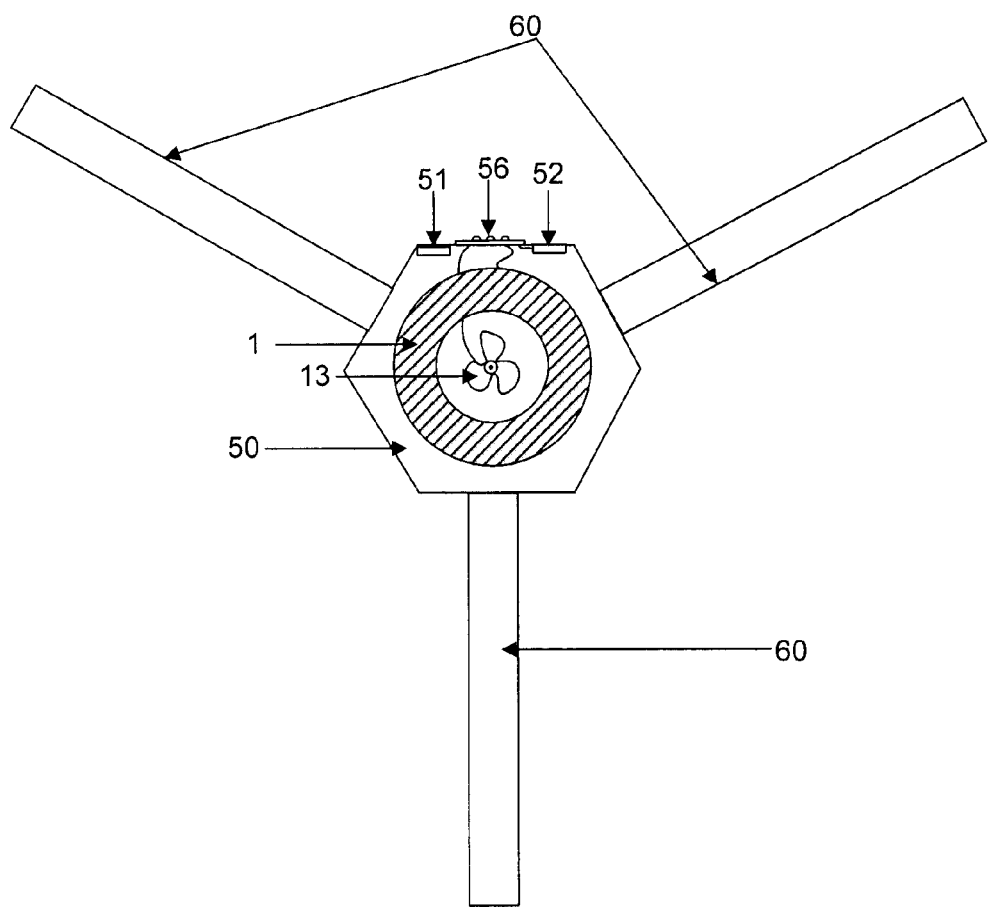
FIG. 6 is a bottom view of an alternate stand embodiment of the invention.

In an embodiment, the invention comprises a tree stand 50. The stand may have legs (FIG. 6) or be a solid shape, but any shape that supports the tree without the danger of tipping can be used for the stand. The stand is formed from any rigid material (similar to the disk, such as metal polymer and composites thereof). As shown in FIG. 5, the stand comprises a motorized fan 13 positioned to force air through the tree trunk. The fan also operates to lower the temperature of the heaters attached to the disk, whether located in the stand or in the trunk. The top of the stand is open and interconnectable to the trunk piece of an artificial tree, such that when the fan operates, air is blown up the trunk and flows through disks located between each trunk section so that fragrance is dispensed. The air is forced though disks containing fragrance cartridges. The disks may be placed at the opening of the bottom of the trunk, and/or between the sections of the trunk. The fragrance is omitted from the openings in the disk and/or holes 32 in the trunk.

As depicted in FIG. 5, the stand comprises elements that are typically used at Christmas, such as lighting 51, audio 52, a mechanism to rotate the tree on a vertical axis 53, clamps to secure the trunk 54, and a timer 55. The elements are electrically connected to a control panel 56 and an energy source 57 that controls the elements individually or together. Lighting is such as that used on a Christmas tree, a rotating color wheel that projects light on or from the tree or stand, twinkle lights, and the like. Audio is recorded music or voice, or an electronic chime or digital chip with an amplifier and a speaker. When activated, the audio reproduces musical tones, a melody, a song, chimes, a recorded voice or other sounds. The control panel has on/off switches. The control panel of the stand is connected to the electrical power or batteries. The timer that allows a user to set a desired time of operation for the chime/music, the fan, lights and/or the heater. The stand optionally includes a compartment for storing replacement fragrance cartridges. In an embodiment, the disk includes all of the elements. In an embodiment depicted in FIG. 6, the present invention is a tree stand 50 has three or more legs 60.

In an embodiment, more than one disk is used on a tree. For example, three scented disks are inserted into corresponding slots incorporated between or within the pole or trunk of the tree and the stand. The segments of trunk or the disks themselves are connected to one another through plugs and wires. The trunk slots are strategically positioned for ease when replacing the fragrance cartridges. The trunk of the tree or the stand incorporates holes through which the scent emits into the surrounding area. A section of wire featuring a male plug extends from the lowest slot and is inserted into a female outlet of a light strand, extension cord, or within a standard wall outlet. In an embodiment, the device includes a timer so that a user may active the heater during selected times. The fragrance cartridge is impregnated with a volatile essential oil. When plugged in, the heater warms the fragrance cartridge scent molecules to a sufficient vapor pressure and a scent is emitted. In an embodiment, a fragrance cartridge is disposable and lasts for approximately 30 to 45 days, depending on the usage.

In an embodiment using a pine scent, the invention would provide the smell of a live tree for the artificial tree. When used, the invention fills the area with a pleasing aroma that may affect an individual's mood. By dispensing a scent, the invention adds to the holiday ambiance. In an embodiment, the invention is included in an artificial tree that mimics a Scotch pine, natural balsam, flocked balsam, Canadian pine, tiered blue spruce, tiered forest green spruce, or Kris Kringle fir.

Different scents may be used with different trees, especially those having a theme, such as candy ornaments, fruit, color and the like. The invention uses a wide array of scents, including but not limited to pine, cinnamon, apple, sugar cookie, pumpkin, mistletoe, peppermint, bayberry, rose, rain, lilac, chamomile, eucalyptus, ylang ylang, vanilla, orange, lemon, nutmeg, and the like. The scents are concentrated. Various fragrances stimulate neurotransmitters in the brain to generate pleasant sensations throughout the body, reduce pain, stimulate appetite, arouse sexual feelings, reduce stress, and generate an overall sense of well being. Chamomile is designed to induce a restful sleep as it calms and soothes individuals. Eucalyptus invigorates and stimulates individuals. The scent of lemon also invigorates individuals while also bringing optimism and clarity. Similar effects are produced by the scent of peppermint which revitalizes and energizes while also stimulating the mind. The fragrance of a rose is thought to inspire warm emotions while also relieving tension. Finally, the scent of ylang ylang inspires creativity, sensuality, and openness while also easing depression.

In an embodiment, the invention is incorporated within the design of artificial wreaths, garland, and other holiday decorations.

In an embodiment, the invention is produced as part of an artificial tree. The needles of the tree are produced from flame resistant polyvinyl chloride, and a steel pole covered with green vinyl is used for the trunk. The disk and the stand are produced from an injection molded plastic or a die cast metal. In an embodiment, the slots of the trunk containing the scent disk are connected by an electrical wire. Holes are incorporated throughout the trunk through which the aroma passes. In an embodiment, the scent disks are packaged and included in the artificial tree.

The foregoing descriptions of specific embodiments and examples of the present invention have been presented for purposes of illustration and description. They are not intended to be exhaustive or to limit the invention to the precise forms disclosed, and obviously many modifications and variations are possible in light of the above teachings. It will be understood that the invention is intended to cover alternatives, modifications and equivalents. The embodiments were chosen and described in order to best explain the principles of the invention and its practical application, to thereby enable others skilled in the art to best utilize the invention and various embodiments with various modifications as are suited to the particular use contemplated. It is therefore to be understood that within the scope of the appended claims, the invention may be practiced otherwise than as specifically described herein.

I claim:

1. A scent dispersing artificial tree comprising:
   a pole, the pole a hollow structure and comprising at least two sections secured together to form a trunk of the scent dispersing artificial tree;
   at least one compartment, the at least one compartment located between the at least two sections of the pole;
   at least one disk, the at least one disk comprising a hollow container for housing a replaceable fragrance cartridge, the at least one disk having openings to allow a fragrance to disperse from the at least one disk, the at least one disk located in the at least one compartment; and
   an energizable heater in communication with the replaceable fragrance cartridge such that when the energizable heater is energized, the replaceable fragrance cartridge emits the fragrance.

2. The device of claim wherein a first disk is located in a first compartment between a first and second section of the pole and a second disk is located in a second compartment between the second and a third section of the pole.

3. The device of claim 2 wherein the first disk and the second disk are electrically connected to one another.

4. The device of claim 1 further comprising an energizable fan that, when energized, blows the fragrance out of the at least one disk having openings.

5. The device of claim 4 further comprising one or more elements selected from the group: energizable illuminating source, energizable audio producer, an energy source, and a mechanical rotator, the one or more elements connected to a controller and a timer.

6. The device of claim 1 further comprising a stand having an opening for receiving a bottom end of the pole, the stand comprising an energizable fan that, when energized, blows air through the pole, the fragrance is blown out of the at least one disk having openings.

7. The device of claim 6 wherein an additional disk is located in a first compartment at the bottom end of the pole when placed in the stand, the first compartment in addition to the at least one compartment, and the at least one disk is placed in the at least one compartment between the at least two sections of the pole.

8. The device of claim 6 further comprising at least one element selected from the group of an energizable illuminating source, an energizable audio producer, an energy source, and a mechanical rotator, the at least one element connected to a controller and a timer.

9. The device of claim 6 further comprising a container for holding replacement cartridges.

10. The device of claim 6 wherein the pole comprises multiple holes to allow the fragrance to emit from the pole.

* * * * *